United States Patent [19]

Harrison et al.

[11] Patent Number: 4,661,068
[45] Date of Patent: Apr. 28, 1987

[54] PARTIAL DENTURE ATTACHMENT APPLIANCE

[76] Inventors: John W. Harrison, R.D. #2, Stoltz Rd., Saegertown, Pa. 16433; John H. Tucker, 1509 Pasadena Dr., Erie, Pa. 16505

[21] Appl. No.: 710,478

[22] Filed: Mar. 11, 1985

[51] Int. Cl.[4] .......................................... A61C 13/22
[52] U.S. Cl. .................................................. 433/181
[58] Field of Search ............... 433/180, 181, 182, 183, 433/184

[56] References Cited

U.S. PATENT DOCUMENTS

| | | |
|---|---|---|
| 1,218,033 | 3/1917 | Yirikian . |
| 1,288,655 | 12/1918 | Nishi . |
| 1,297,199 | 3/1919 | McAuley . |
| 1,297,561 | 3/1919 | Guntner ............................ 433/181 |
| 1,324,476 | 12/1919 | Supplee . |
| 1,664,726 | 4/1928 | Adler . |
| 1,753,644 | 4/1930 | Burdew ............................ 437/181 |
| 3,171,202 | 3/1965 | Lasky . |
| 3,344,842 | 10/1967 | Cameron . |
| 3,787,975 | 1/1974 | Zuest . |
| 3,868,776 | 3/1975 | Lasky . |
| 3,955,280 | 5/1976 | Sneer . |
| 3,955,282 | 5/1976 | McNall ............................... 433/9 |
| 4,193,194 | 3/1980 | Dalise . |
| 4,196,516 | 4/1980 | Poveromo . |
| 4,259,073 | 3/1981 | Emmons . |
| 4,362,509 | 12/1982 | Sulc . |
| 4,380,435 | 4/1983 | Raeder et al. . |
| 4,445,861 | 5/1984 | Klepacki . |
| 4,474,499 | 10/1984 | Pedrazzini . |

FOREIGN PATENT DOCUMENTS

| | | | |
|---|---|---|---|
| 500392 | 6/1928 | Fed. Rep. of Germany | ...... 433/180 |
| 587534 | 9/1932 | Fed. Rep. of Germany . | |
| 2085303 | 4/1982 | United Kingdom | ................ 433/181 |

OTHER PUBLICATIONS

"Introducing The Preci-Vertix Hood", Preat Corporation, copyright 1981, Alphadent p.v.b.a.
"Preci-Vertix", Preat Corporation, copyright 1981, Alphadent p.v.b.a.
APM-Sterngold, procedure manual.
APM-Sterngold, "A Chairside Guide to Stern Attachments in Partial Dentures", copyright 1982.
APM-Sterngold, "Stern JMS Jacket Maintenance System", copyright 1983.
Cendres & Métaux, S.A., "The Resilient Hinge Joint DALBO".
Sterngold, "Coping", copyright 1980.
Barrick, "Recent Advances in Etched Cast Restorations", Journal of Prosthetic Dentistry, Nov. 1984, pp. 619–623.
Day and Best, "Understanding the New Acid–Etch Bridgeword Technique", Laboratory Techniques, Apr. 1984.
Maryland Bridge and Crown Technique; 1982-1983.

*Primary Examiner*—Robert Peshock
*Attorney, Agent, or Firm*—Body, Vickers & Daniels

[57] ABSTRACT

An attachment appliance for a removable partial denture, having complementary male and female interlocking members wherein the male member is bonded to a face of an abutment tooth within an oral cavity. The female member may be removably mounted in a mounting cavity in the removable partial denture.

2 Claims, 12 Drawing Figures

PARTIAL DENTURE ATTACHMENT APPLIANCE

BACKGROUND OF THE INVENTION

The present invention relates generally to dental prostheses, and more particularly, to an attachment device for removable partial dentures and a method of affixing the attachment device within an oral cavity.

In the replacement of several teeth within the mouth, it is often desirable to use a removable partial denture. The removable partial denture is indicated where the arrangement of remaining teeth in the oral cavity cannot support a fixed partial denture. To be retained in position while in use in the wearer's mouth, the partial bridge must be anchored in some manner within the mouth, and is generally removably attached to the remaining teeth.

In the past, two basic types of anchoring attachments have been used. First, extracoronal attachments on the denture, such as clasps, have been used to grip around remaining, abutting natural teeth. In this type of attachment, clasps are provided on the portion of the partial denture closest to the remaining teeth when mounted. In use, the clasps tightly grip the abutment teeth to maintain the connection between the partial denture and abutment teeth, and hold the denture in place. This type of attachment, however, has a particularly unsatisfactory cosmetic appearance, as the clasps, which wrap around the abutment teeth, are visible and unsightly. As an alternative to such extracoronal attachments, many intracoronal attachments have been proposed and used. This type of attachment requires a first member, to be permanently affixed to an abutment tooth, and a complementary second member, releasably interlockable with the first member, mounted on the partial denture. The connecting members are mounted on the partial denture. The connecting members are mounted in their respective positions, generally in close relationship, on abutting surfaces of the abutment tooth and partial denture. This type of connector is much more cosmetically acceptable but the attachment of an extracoronal attachment connector member to the abutment tooth is a difficult procedure. This type of attachment has heretofore required the construction of a crown over the abutment tooth. To make such a crown requires that an otherwise healthy tooth be ground down and reduced in size so that a crown containing the appropriate connector member may be cemented on the remains of the tooth to support the connector member and replace, cosmetically and functionally, the now-destroyed tooth.

The described procedure results in the destruction of an otherwise healthy tooth. Installation of intracoronal attachments is considered a costly and difficult type of dental treatment. Once completed, the destroyed tooth structure cannot be recovered. Additionally, the crowned tooth is still not as cosmetically appealing as an intact natural tooth.

Recent work in the area of fixed partial dentures and tooth replacement has resulted in a new type of restorative method, known as the Acid Etched Resin Bonded Retainer Technique. This method of restoration involves the resin bonding of a framework carrying replacement teeth, to abutting teeth, with a minimum of tooth removal. Thus, fixed partial denture bridges may be permanently attached to the remaining teeth, without the use of crowns, and the concurrent destruction of healthy teeth.

SUMMARY OF THE INVENTION

The present invention overcomes the problems inherent in the prior art attachments, and provides an attachment which is cosmetically appealing, requires no tooth destruction, and provides for secure positioning of the removable partial denture, that is economical to manufacture and install in an oral cavity.

In accordance with the present invention, a removable partial denture attachment is provided by a first member having a connector portion and a contoured mounting element resin bonded to an abutment in the oral cavity, a complementary second member interengaging with the first member on the removable partial denture to maintain the disposition of the denture in an oral cavity.

In accordance with a further aspect of the present invention, the complementary members of the connecting pair are also constructed as to allow for freedom of movement at the interengaging portions to prevent destructive stress on the resin bonded connection.

In accordance with another aspect of the invention, one of the members is a generally elongated, slotted tube disposed generally vertically and perpendicularly with respect to the gingival portion of the oral cavity, in the partial denture, and extending substantially into the denture, and of a length which precludes impingement in the vertical direction on the connector portion when vertical forces are exerted on the partial denture.

In accordance with yet another aspect of the invention, the connector portion is ball shaped for slidable insertion into the female slotted tube, whereby the joint allows substantial rotational movement in the lateral direction, slidable movement in the vertical direction, and combinations of rotational and slidable movements.

In accordance with another aspect of the invention, the second member may be of a plastic material, and be removably insertable within a processed mounting cavity in the partial denture, to provide for replacement of the second member upon wear or damage.

In accordance with another aspect of the invention, a method for mounting a partial denture attachment appliance within an oral cavity is provided including the steps of providing a male form member to make a member with an attachment contoured to the shape of an abutment and suitable for bonding to the face thereof; preparing the abutment and attachment portion for bonding; bonding the attachment portion to the abutment; and providing a female receiving member in a partial denture, the female receiving member having a suitable shape and location to be removably interlockable with the male member when the partial denture is operationally inserted into the oral cavity.

In accordance with yet another aspect of the present invention, a kit is provided comprising a first member form for forming a first member adapted to be bonded to an abutment and a second member for insertion into partial denture to receive said first member in an interengaging fashion.

The primary object of the present invention is to provide a removable partial denture attachment in an oral cavity allowing a secure fit, a minimum of tooth destruction and a pleasing cosmetic appearance.

Another object of the invention is provision of a removable partial denture attachment having a male member bonded extracoronally to an abutment within the oral cavity, and a complementary female member provided in a partial denture.

Another object of the invention is to provide a male member and complementary female member suitable for use in a bonded attachment. In accordance with this object, the ball shaped male member is provided for insertion into a tube shaped receiving portion of the female member to provide for slidable vertical motion, and rotational lateral motion, or combination thereof, between the members, thereby minimizing the mechanical stresses on the connection.

Another object of the invention is to provide a method for mounting a removable partial denture attachment appliance in an oral cavity and on a partial denture, which provides both for a permanent attachment within the oral cavity, and an easily replaceable attachment structure in the removable partial denture.

Another object of the invention is that the first member may be formed by either a precious or non-precious metal.

Another object of the invention is to provide a kit from which such a partial denture attachment may be made.

These and other objects and advantages will become apparent from the following description used to illustrate a preferred embodiment of the invention and read in connection with the accompanying drawings in which.

Figure 1:
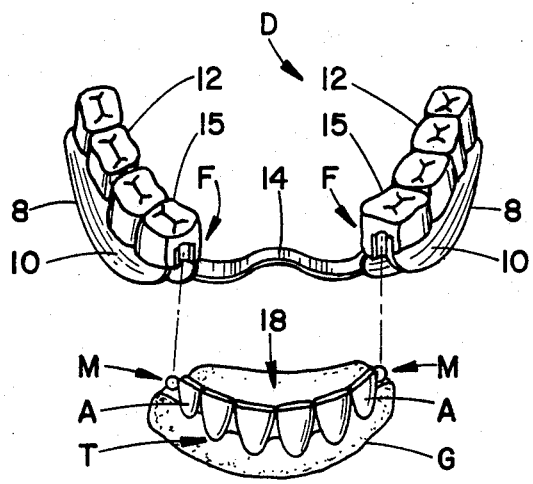
FIG. 1 is an exploded perspective view of lower natural teeth and a dental prosthesis illustrating a preferred embodiment of the invention.
Figure 2:
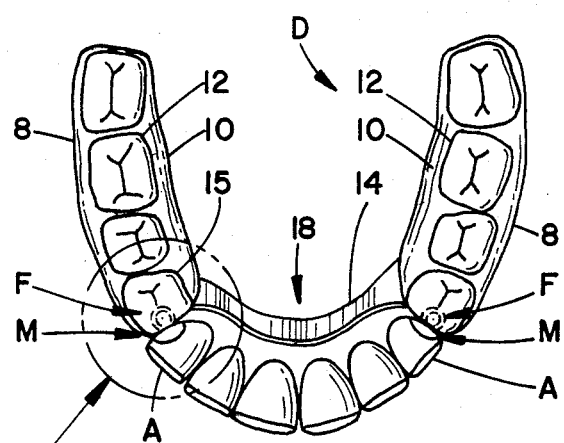
FIG. 2 is a plan view of a set of lower teeth with prosthesis attached.

Referring now to the drawings, wherein the showings are for the purpose of illustrating a preferred embodiment of the invention only and not for the purpose of limiting the same, FIGS. 1 and 2 shown a plurality of teeth T, a gingival portion of G and a removable partial denture D to be removably attached to teeth T by male member M on teeth T and female member F and the partial denture D.

Natural teeth T are embedded in the gingival portion G of an oral cavity and are generally comprised of several adjacent teeth grouped together. The tooth to which the device will be attached at either end of the group of teeth is referred to as abutment tooth A, which will form the anchoring point for the partial denture D.

Partial denture D is generally comprised of two denture portions 8, each having a saddle portion 10, denture teeth 12, and a direct retainer 14. Each side is generally similar, so that only one side will be discussed. The saddle portions 10 have a generally contoured and concave seat to fit the gingival portion G of the oral cavity, where natural teeth have been removed. Denture teeth 12 are teeth substitutes, simulating the original, removed teeth in form and function to as great an extent as possible, and provide a denture abutment tooth 15 facing abutment tooth A. Direct retainer 14 joins the two denture portions 8 across an interior side 18 of the natural teeth T in the oral cavity, thereby forming a single unit which is too large to be swallowed by the wearer. These elements are typical of removable partial dentures and, while not forming a novel part of the invention, demonstrate the environment in which the invention is used.

Figure 3:
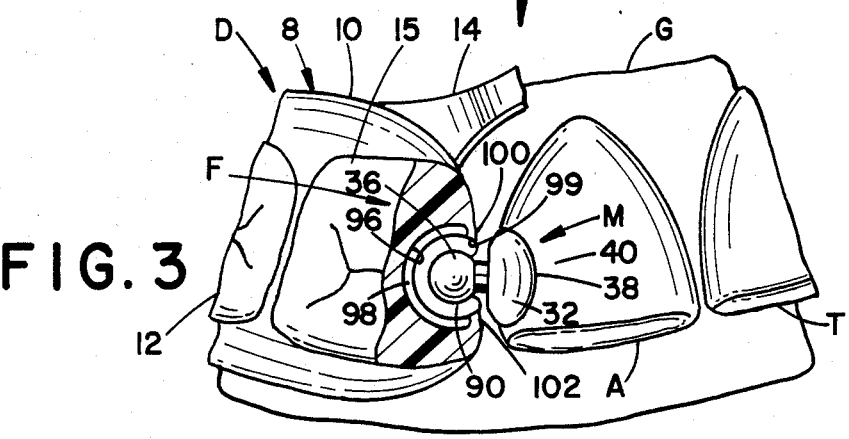
FIG. 3 is an enlarged view partially in section of the circled portion of FIG. 2, showing one attachment means.
Figure 4:
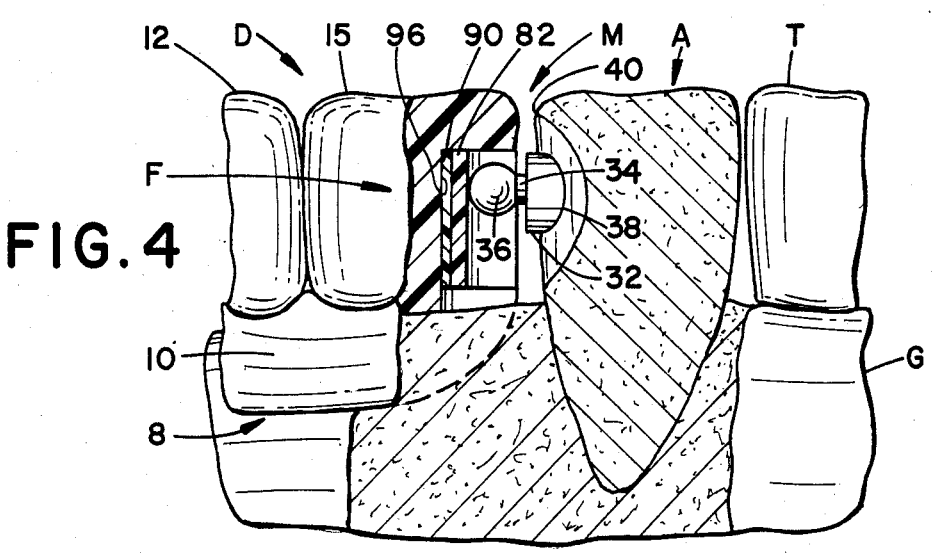
FIG. 4 is a front view of FIG. 3, partly in section.

FIGS. 3 and 4 best demonstrate the orientation of the novel partial denture attachment in conjunction with its environment. Male member M has a mounting portion 32, a shaft member 34, and a connector ball member 36. The mounting portion 32 has a mounting face 38 generally contoured in shape corresponding to the face 40 of the abutment tooth A to which it will be permanently affixed. Connector ball member 36 is generally spherical in shape having a portion thereof cut off and attached to the shaft member 34, which connects the connector ball member 36 to the mounting portion 32. Shaft member 34 is generally cylindrical in configuration.

While it may be recognized that the male member M must be generally of a size suitable for use in the wearer's oral cavity, variations in size are possible. In practice, the spherical portion of the connector ball member 36 has a diameter approximately 0.067" and extends outwards from the shaft approximately 0.045". The cylindrical shaft portion 34 has a diameter of approximately about 0.040" and a length of approximately 0.020". The actual size of the mounting portion 32 of the male member M to be attached to the abutment tooth A will vary as discussed hereinbelow.

Figure 7:
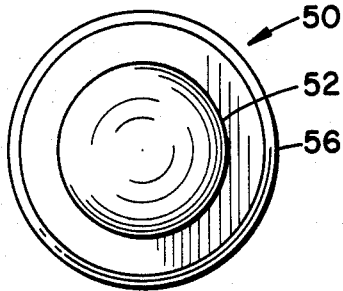
FIG. 7 is a left end view of the male attachment element form.
Figure 5:
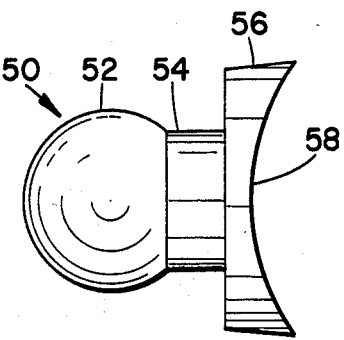
FIG. 5 is a front view of the male attachment element form.
Figure 6:
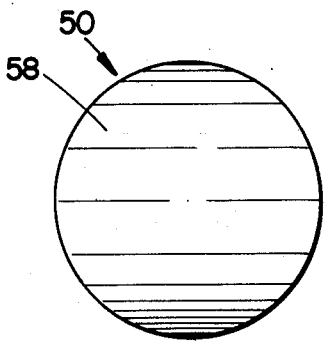
FIG. 6 is a right end view of the male attachment element form.

In practice, a male member form 50, shown in FIGS. 5, 6 and 7, made of plastic or nylon material and having the same general shape as that of the male member M is supplied to a dentist as a form to construct an exact fitting male member M to be installed into the oral cavity. The male member M may be formed from precious or non-precious metal and cast to an appropriate form by a lost-wax process, whereby a mold is created using standard male member form 50, having connector ball form 52, shaft form 54 and mounting portion form 56, after the dentist or prosthodontist shapes a form to provide an appropriately shaped mounting face form 58. A mold is formed from the male member form 50 and shaped mounting face form 58, the form material is burnt out of the investment (mold), and replaced with a suitable metal which, on hardening, forms the actual male member M to be attached to the abutment tooth face 40. Lost wax process molding of this type is well known in the dental art.

The male member M is attached to the abutment tooth face 40 generally along the lines taught by Acid Etched Resin Bonded Retainer Technique. It is a feature of this method that an absolute minimum of abutment tooth enamel is removed, with the potential for no removal at all. The mounting surface 40 of the abutment tooth A is etched with a 30% to 40% phosphoric acid solution and then cleaned and dried. Mounting face 38 of the male member M, which will contact the tooth, is also chemically etched with an appropriate acid solution. The mounting face 38 is then bonded to the prepared abutment tooth face 40 with a enamel bonding agent, generally comprised of a combination of an unfilled resin and a luting composite resin. Male member M is cemented securely in place, on the abutment tooth A in the oral cavity.

Figure 9:
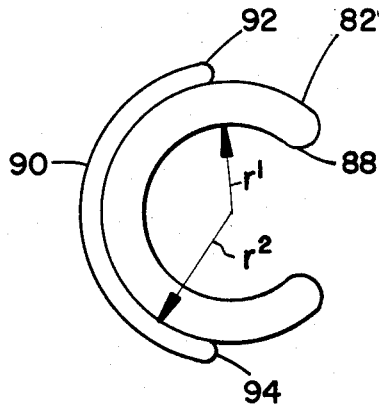
FIG. 9 is a left end view of a female attachment element.
Figure 8:
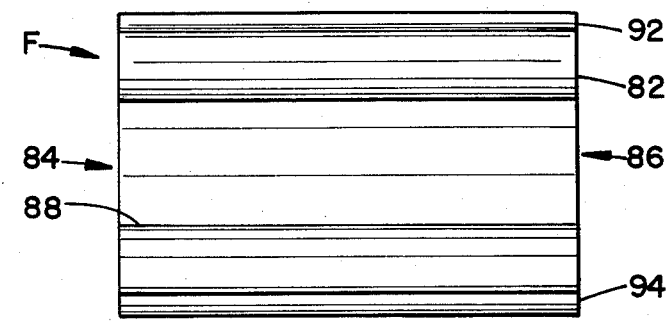
FIG. 8 is a front view of a female attachment element.

Complementary female member F is oriented in the denture portion and shown in FIGS. 1 and 2. The female receiving member F best shown in FIGS. 8 and 9 is comprised of a generally cylindrical, elongated tube member 82 opened at first end 84 and the second end 86 having a receiving slot 88 extending the length of tube 82. A retaining member 90 is provided on the exterior of the female member F, comprised of raised lip members 92 and 94, disposed on either side of slot opening 88, and extending the length of tube member 82. In a preferred embodiment, the female receiving member F may be of plastic or nylon material.

In use, female receiving member F is mounted in receiving cavity 96 formed in partial denture portion 8. Mounting cavity 96 is formed in denture abutment face 98 of the denture portion 8, which will be adjacent to tooth abutment face 40, which supports male member M, when the partial denture D is inserted in operational relationship to the natural teeth T in the oral cavity. The mounting cavity 96 is contoured to the general size and shape of the female receiving member F, having an appropriate mounting opening 99 in the denture abutment face 98 to present the receiving slot opening 88 to face the male member 30. The cavity also provides cooperating retainers 100 and 102, which, in combination with lip members 92 and 94 prevent tube member 82 from rotating within cavity 90 and maintain the slot 88 in an appropriate position for attachment to the male member 30.

Female member F and mounting cavity 96 extend through the saddle portion 10 and generally vertically into the abutment denture tooth 15. For relief of shear stress on the connection of the male member M to the abutment face 40, it is preferable that there be no impingement of any surfaces on the connector ball 36 in the vertical plane. When inserted into the female member F, the connector ball 36 will be maintained generally in the mid-section of the tube member 82, with a range of vertical motion therethrough determined by the motion of denture portion 8 within the oral cavity, and, for example, the fit of the denture, gum condition or bite of the wearer. The amount of motion anticipated by the dentist or prosthodontist will determine the length of the tube 82 in cavity 96. Such length may extend vertically through the denture portion 8, or only a portion thereof, with the material of the denture tooth enclosing the mounting cavity 96 and tube end 86, but providing end 84 to remain open for insertion of the male member connector ball 36.

As discussed with respect to male member M, female receiving member F and accordingly, the mounting cavity 96 will vary in size in accordance with the needs of the wearer. Tube member 82 has an interior radius $r^1$ which will allow the interior of the tube to frictionally engage the connector ball member 36, but allow slidable motion between the tube and ball in the vertical direction when the wearer is chewing or otherwise creating vertical forces on the denture portion 8. The combination of the tube 82 and ball 36 will also allow some rotational motion of the ball within the tube to further relieve connection stress in lateral directions. Thus, the connector ball 36 acts as a ball joint connector, and slidable retainer when in place in the female receiving member F.

It is contemplated that during the movement and continued use of a metal ball connector 36, the plastic female member F will eventually wear, loosening the frictionally engaging fit between the two members. Accordingly, in a preferred embodiment of the invention the female member F may be inserted into and out of the mechanical engagement in the mounting cavity 96 for replacement purposes. In view of the requirements of the invention, the tube member 82 may have an interior tube radius $r^1$ of approximately 0.0335", an exterior tube radius $r^2$ of approximately 0.0535", a slot opening 88 having a width of approximately 0.043", retaining member 90 having lips 100, 102 extending about 0.020" outwardly from the exterior tube diameter and wrapping around the circumference of the tube 82, generally about less than 180°. The length of the female member is adjustable by the dentist or prosthodontist according to the size of the denture abutment tooth 15 but the length of the supplied size of the female receiving member F may be approximately 0.196". In this example, a dentist or prosthodontist would be required to construct a denture portion 8 with the mounting cavity 96 corresponding in shape and fit to the female member F and having a radius of about approximately 0.065" to accomodate the exterior of retainer 90, and radius of about 0.055" through the remainder of the cavity to correspond to the outer diameter $r^2$ of the tube 82. The length of mounting cavity 96 corresponds to the length of the female member F. Slot opening 88 of female member F will be approximately 0.043", or wide enough for some movement of the shaft member 34, within the slot, to allow the male member M to serve its function as a ball joint connection.

In accordance with the above description, when the female member F is fixed securely into position in the mounting cavity 90 in denture portion 8, the partial denture D is inserted into position in the gingival portion G of the oral cavity. The saddle portion 10 is positioned onto the gingival portion to where natural teeth have been previously removed, and with the direct retainer 14 abutting the interior side 18 of the remaining natural teeth T. First opening 86 of the tube member 82 and saddle portion 10 is inserted over ball member 36 with the shaft 34 slidably fitting into the slot opening 88 in the female member F. As the saddle portion 10 of the denture D is inserted firmly against the gingival portion G, the female member F slidably receives the male member M. Thus, the male member M firmly holds denture portion 8 in place against the gingival portion G of the oral cavity adjacent abutment tooth A, in a manner which allows some degree of movement, between the attachment members, but prevents the destruction of the connection between the male member 30 and the abutment tooth face 40.

The disclosed attachment may take many forms and sizes as the fitting of dentures and partial dentures is a customized procedure. The final product will be the best solution for the requirements of a particular oral cavity and patient. Accordingly, it is an advantage of the present device, that, while affording to the dentist the option of creating a permanent extracoronal attachment in the oral cavity, the same male form 50 and female member F may be used advantageously in conjunction with a crowned tooth for formation of an extracoronal attachment. In such an application, rather than using the male form 50 to make a mold, and cast a mounting portion 56 and mounting face 58 for bonding to the abutment tooth face 40, the same form 50 may be used in the casting of a crown so that permanent crown attachment may be attached to a ground down tooth or implant.

Figure 11:
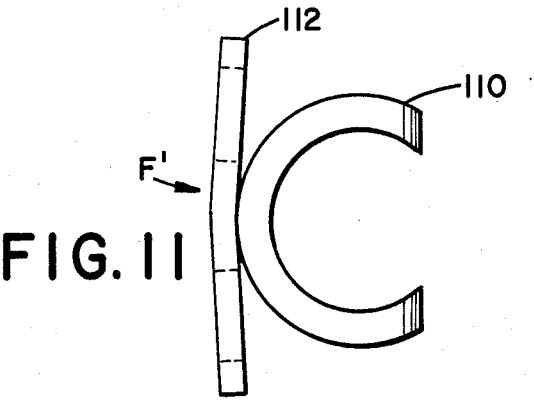
FIGURE 11 is a top view of the alternative embodiment of the female attachment element.
Figure 12:
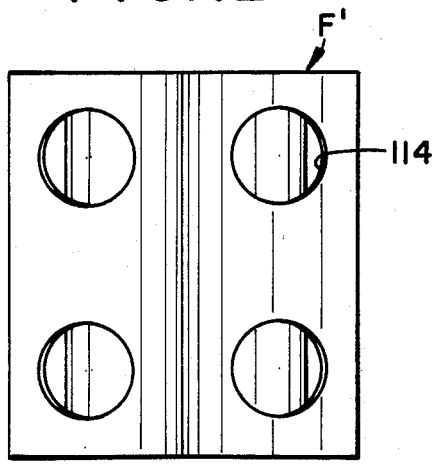
FIG. 12 is a left end view of the alternative embodiment of the female attachment element.
Figure 10:
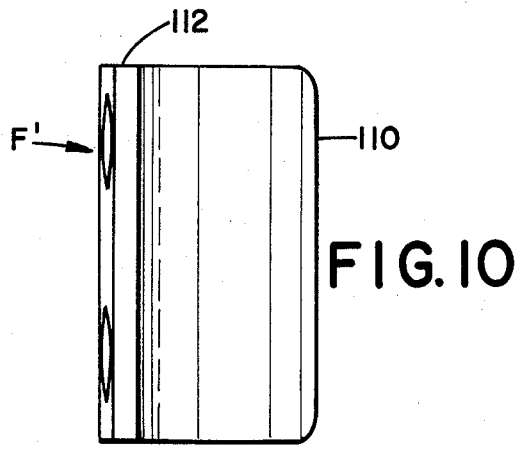
FIG. 10 is a side view of the alternative embodiment of the female attachment element.

The female member F may also be altered to particular applications or problems. In accordance with another embodiment of the invention, shown in FIGS. 10, 11 and 12, the female member F' may be comprised of a tube 110 and wing extension 112. The wing extension 112 is adapted to be permanently mounted within the denture tooth rather than slidably removable as in the previous embodiment. Perforations 114 are provided within the wing 112 to allow the flow of the denture tooth forming material, or adhesive material through the wings 112 to hold it permanently in place. While, as discussed above, it is expected that the male member 30 will be of metal construction, and that the female member will wear in use, it is possible to also make the female member a metal material, with the expection of replacement, or with a coating to prevent wearing friction. Alternatively, the female member F' may be of a larger size to slidably receive a plastic insert member, the sleeve being replaceable on wearing.

It is contemplated that the present invention will find particular and preferred use in conjunction with bonding the male member M to a natural abutment tooth A. However, it will be appreciated that the member may be bonded or affixed to any permanent, abutment member within an oral cavity, and such members are considered interchangeable with natural teeth.

The invention has been described with reference to the preferred embodiment. Obviously, modifications and alterations will occur to others upon the reading and understanding of this specification. It is intended to include all such modifications and alterations insofar as they come within the scope of the appended claims or the equivalents thereof.

Having thus described the invention, it is claimed:

1. An appliance for attaching a removable partial denture to an abutment tooth within an oral cavity, said partial denture having a concave support portion receiving and supported by a gingival portion of said oral cavity, and a tooth portion simulating the appearance and operative characteristics of natural teeth, said appliance comprising:
    (a) a male attachment member having an attachment portion with a surface contoured to match an exterior surface of said abutment tooth and adapted to be permanently adhesively bonded onto said exterior surface of said abutment tooth, a shaft portion and a ball shaped connector member;
    (b) an elongated slotted receiving cavity adjacent a face of said partial denture proximate to said abutment tooth, said cavity being oriented in a vertical plane and extending through said concave support portion substantially into said denture and having a vertically orientated slot, a first open end for receiving said connector member and a closed second end spaced from said first open end and adapted to be maintained in spaced relationship with said connector member; and,
    (c) a resilient slotted cylindrical tube member mounted in said receiving cavity having its slot aligned with the slot of said receiving cavity, said resilient slotted cylindrical tube member receiving said connector member in slidable engagement therewith.

2. A device as defined in claim 1 wherein said resilient tube is provided with retainer lip means interacting with retainers in said retaining cavity to mechanically retain said resilient tube in position in said receiving cavity and prevent rotation of said tube in said receiving cavity.

* * * * *